United States Patent [19]

Shibata et al.

[11] 4,301,148

[45] Nov. 17, 1981

[54] ANTICOCOIDIAL DRUG

[75] Inventors: Kenji Shibata, Ohi; Masami Ozima, Kawagoe, both of Japan

[73] Assignee: Nisshin Flour Milling Co., Ltd., Tokyo, Japan

[21] Appl. No.: 189,219

[22] Filed: Sep. 22, 1980

[30] Foreign Application Priority Data

Sep. 29, 1979 [JP] Japan .............................. 54-124726

[51] Int. Cl.³ .......................................... A61K 39/012
[52] U.S. Cl. ...................................... 424/93; 424/88
[58] Field of Search ................................... 424/88, 93

[56] References Cited

PUBLICATIONS

Millard et al., Vet. Bull. 44 #5995(1974), Int. J. Parasitology 4(4): 423–432 (1974), The Viability and Survival of Sporozoites of Eimeria in Vitro.

Shirley et al., Vet. Bull. 47 #2620(1977), Parasitology 73(3): 337–341 (1976), Some Observations on the Sexual Differentiation of Eimeria Tenella using Single Sporozite Infections in Chicken Embryos.

Kouwenhoven et al., Vet. Bull. 47 #5598(1977), Veterinary Parasitology (1976), 2(3): 283–292, Demonstration of Circulating Antibodies to Eimerla Tenella by the Indirect Immuno Fluorescent Antibody Test using Sporozoites and Second-Stage Schizonts as Antigon.

*Primary Examiner*—Shep K. Rose
*Attorney, Agent, or Firm*—Haseltine and Lake

[57] ABSTRACT

Newly hatched fowl are inoculated intra-cloacally with an anticoccidial effective amount of sporozoities of *eimeria tenella* to prevent fowl coccidiosis caused by *eimeria tenella*.

1 Claim, No Drawings

ANTICOCOIDIAL DRUG

This invention relates to an anticoccidial drug capable of immunologically preventing fowl coccidiosis and a method of inoculating fowl with said anticoccidial drug.

Fowl coccidiosis is an infectious disease caused by infection of fowl with a certain species of parasitic protozoa and is being widely spread in all parts of the world. Birds and beasts infected with the parasitic protozoa present such symptoms as diarrhea, haemorrhagic faeces, etc. and often fall dead in case where those infected have not been subjected promptly to treatment for alleviating such symptoms or where the symptoms have seriously developed. Thus, coccidiosis is known as a disease that inflicts the largest damage to poultry keepers because infected fowls are hindered in their growth even when they narrowly escaped from death.

Oral administration of drugs including vaccine has heretofore been adopted for the prevention of coccidiosis as referred to above. The vaccine for coccidiosis as referred to herein is intended to designate a mixed liquid composition comprising several kinds of oocysts which are apt to cause coccidiosis, and fowls in poultry farms are orally inoculated with the composition. Such preventive measures as relying on administration of drugs, however, had such drawbacks that the thus administrated drugs gradually lessen their preventive effect as the parasitic protozoa gradually comes to gain and stiffen its resistance to the drugs and the like problems are involved therein. The vaccinal preventive measure also possessed such drawbacks that the duration of immunity is short and no perfect prevention can be expected even during immune period.

The present inventors conducted researches to solve the afore-mentioned problems associated with the prior art preventive measures of coccidiosis and eventually have found that the prevention of fowl coccidiosis can be achieved by inoculating fowls through their cloacae with sporozoites of *Eimeria tenella* which is one of pathogenic protozoa of fowl coccidiosis.

The sporozoite as referred to in the present invention is one form of life cycle of *Eimeria tenella*, said sporozoite being kept alive. Preparation of this sporozoite used in the present invention is illustrated hereinafter.

Sporocysts are obtained by breaking membrane of sporulated oocysts of *Eimeria tenella* isolated from faeces, walls of caecum and contents of caecum of fowl infected with coccidiosis caused by *Eimeria tenella*. Subsequently, the sporocysts thus obtained are treated with fowl's bile and trypsin to effect excystation of sporozoites. The excystation product thus obtained mainly contains sporozoites and, in addition thereto, includes also oocysts and sporocysts, and membranes of oocysts and sporocysts respectively.

Fowls are then inoculated with the sporozoites obtained in the above manner. In practicing the inoculation, the sporozoites are suspended in such buffer as a phosphate buffered saline (PBS) and the resulting suspension is inoculated into fowls orally, muscularly or cloacally. Cloacal inoculation is particularly preferred, wherein the suspension is dropped into fowl's anus or injected into cloaca thereof. Fowls are preferably inoculated with the sporozoites amounting to about 500 in number per fowl.

By virtue of the use of an anticoccidial drug according to the present invention, fowl coccidiosis caused by *Eimeria tenella* can almost perfectly be prevented without bringing about undesirable side reaction. Furthermore, the infection preventing effect of the present anticoccidial drug is markedly prominent, for example, when one-day chicken is inoculated therewith, the effect lasts for a period of more than 11 weeks.

Following examples are given to demonstrate the effect of the present invention.

EXAMPLE 1

Test method

Ten (10) zero-day old chickens (of Hubbard for exclusive use in broiler) are individually inoculated dropwise through anus with a sample mentioned below. Subsequently, the chickens are infected at 21-day old stage with coccidiosis by oral administration of 200,000 sporulated oocysts of *Eimeria tenella* per chicken. The chickens used as control are simply infected likewise but no inoculation is effected thereon. Observation was conducted on the 8th day after infection as to caecum lesions, number of oocysts in faeces, haemorrhagic faeces and mortality to obtain the results as shown in Table 1. Evaluation following the observation was conducted in the manner mentioned below.

SAMPLE

Present invention: 10,000 sporozoites of *Eimeria tenella* were suspended in a phosphate buffered saline (−).

Comparative Example (1): 5,000 sporocysts (calculated as 10,000 sporozoites) of *Eimeria tenella* were suspended in a phosphate buffered saline (−).

Comparative Example (2): 1,250 oocysts (calculated as 10,000 sporozoites) of *Eimeria tenella* were suspended in a phosphate buffered saline (−).

Comparative Example (3): The above-mentioned sample of the present invention was heated at 60° C. for 30 minutes.

Comparative Example (4): 10,000 sporozoites of *Eimeria tenella* were put into a 10% formalin solution, allowed to stand for 30 minutes, followed by centrifugal separation, and the resulting sediment was suspended in a phosphate buffered saline (−).

The oocysts, sporocysts and sporozoites used in the above-mentioned samples, respectively, were prepared according to the procedure described in "J. Protozool," Vol. 9 (2) pages 154–161 (1962) in the following manner. Faeces, walls of caecum and contents of caecum of fowls orally administered with sporulated oocyst of *Eimeria tenella* were collected, floated on a 3% potassium bichromate solution and incubated at 28° C. for 2 days. The thus obtained solution containing sporulated oocysts was subjected to centrifugal separation (at a rate of 3000 rpm for 10 minutes), and the resulting sediment was collected. Subsequently, the sediment thus collected was rinsed with water and charged with a saturated saline solution. The resulting solution was centrifuged (at a rate of 3000 rpm for 10 minutes), the supernatant collected therefrom was diluted with water and further centrifuged (1000 rpm for 3 minutes) to collect the resulting sediment. This sediment almost consisted of oocysts only [the oocysts were used in Comparative Example (2)]. The oocysts thus obtained were charged with water and a 5% sodium hypochlorite solution and allowed to stand for 15 minutes, followed by centrifugal separation (2000 rpm for 3 minutes). The resulting sediment was rinsed with water and then ground with a homogenizer. The ground product thus obtained almost consisted of sporocysts [the sporocysts were used in Comparative Example (1)]. The sporocysts thus obtained were charged with a 5% fowl's bile, 0.25% trypsin and a phosphate buffered saline (—), followed by digestion in a hot water bath at 40° C. for about 1.5 hours. The digestive liquid thus obtained was subjected to centrifugal separation to collect a sediment, and the thus collected sediment was rinsed with a phosphate buffered saline (—). The sediment thus treated almost consisted of sporozoites (the sporozoites were used in the present invention).

Evaluation method

Caecal lesion: Degrees of caecum atrophy and haemorrhage, and amounts of inflammatory exudate are represented thereby.
+++: Heavy
++: Medium
+: Slight
⊥: Very slight
—: None
Haemorrhagic faeces: Evaluation is made in accordance with the method adopted for caecal lesion.
Number of oocysts in faeces: The number of oocysts in 1 g of faeces is represented thereby.

TABLE 1

|  | Caecal lesion | | | Haemor-rhagic faeces | Number of oocysts per gram in faeces ($\times 10^4$ pieces) | Mortality (%) |
| --- | --- | --- | --- | --- | --- | --- |
|  | Atrophy | Haemorrhage | Exudate |  |  |  |
| Present invention | ⊥ | ⊥ | ⊥ | ⊥ | 0 | 0 |
| Comparative Example (1) | +++ | + | ++ | + | 6 | 10 |
| Comparative Example (2) | +++ | + | +++ | + | 15 | 30 |
| Comparative Example (3) | +++ | ++ | + | + | 85 | 80 |
| Comparative Example (4) | +++ | + | ++ | ++ | 5 | 20 |
| Control | +++ | +++ | +++ | ++ | 117 | 70 |

EXAMPLE 2

Test method

Ten (10) chickens (the same as used in Test Example 1) were individually inoculated with the undermentioned samples, respectively, in the manner as indicated below. The chickens were infected in the same manner as in Test Example 1 and observation was conducted likewise. The chickens used as control were not inoculated with the samples but merely infected in the same manner as in Test Example 1. The results obtained were as shown in Table 2, wherein the same evaluation method as in Test Example 1 was adopted.

Samples and Inoculation

Present invention (1): 10,000 sporozoites per fowl were inoculated on fowl's anus.

Present invention (2): 10,000 sporozoites per fowl were orally inoculated.

Present invention (3): 10,000 sporozoites per fowl were injected through fowl's pectoralis.

Comparative Example: 1,250 oocysts per fowl were orally inoculated.

The sporozoites and oocysts used as samples were prepared in the same manner as in Example 1.

TABLE 2

|  | Caecal lesion | | | Haemorrhagic faeces | Number of oocysts in faeces ($\times 10^4$ pieces) |
| --- | --- | --- | --- | --- | --- |
|  | Atrophy | Haemorrhage | Exudate |  |  |
| Present invention (1) | ⊥ | ⊥ | ⊥ | — | 0 |
| Present invention (2) | ++ | + | + | + | 5 |
| Present invention (3) | ++ | + | ++ | + | 8 |
| Comparative | +++ | ++ | +++ | ++ | 5 |
| Example Control | +++ | +++ | +++ | ++ | 117 |

What we claim is:

1. In a method for preventing fowl coccidiosis caused by *Eimeria tenella*, the improvement which comprises inoculating newly hatched fowl through the cloaca with an anticoccidial intra-cloacally effective amount of from 500 to 10,000 sporozoites of *Eimeria tenella* suspended in a suitable buffered saline carrier.

* * * * *